United States Patent
Haga et al.

(10) Patent No.: US 9,984,907 B2
(45) Date of Patent: May 29, 2018

(54) EVACUATION METHOD AND VACUUM PROCESSING APPARATUS

(71) Applicant: Tokyo Electron Limited, Tokyo (JP)

(72) Inventors: Hirofumi Haga, Miyagi (JP); Nobutaka Nakao, Miyagi (JP); Hideaki Yakushiji, Miyagi (JP)

(73) Assignee: Tokyo Electron Limited, Tokyo (JP)

( * ) Notice: Subject to any disclaimer, the term of this patent is extended or adjusted under 35 U.S.C. 154(b) by 0 days. days.

(21) Appl. No.: 14/977,778

(22) Filed: Dec. 22, 2015

(65) Prior Publication Data
US 2016/0189988 A1 Jun. 30, 2016

(30) Foreign Application Priority Data
Dec. 25, 2014 (JP) .................. 2014-263378

(51) Int. Cl.
*H01L 21/67* (2006.01)
*H01J 37/32* (2006.01)
*A61L 2/24* (2006.01)
*A61L 2/14* (2006.01)

(52) U.S. Cl.
CPC .......... *H01L 21/67069* (2013.01); *A61L 2/14* (2013.01); *A61L 2/24* (2013.01); *H01J 37/32449* (2013.01); *H01L 21/67017* (2013.01); *H01J 37/32834* (2013.01); *Y10T 137/0379* (2015.04); *Y10T 137/86002* (2015.04);
(Continued)

(58) Field of Classification Search
CPC ........ A61L 2/14; A61L 2/24; H01J 37/32449; H01J 37/32834; H01L 21/67069; Y10T 137/86083; Y10T 137/0379; Y10T 137/86027; Y10T 137/86002
See application file for complete search history.

(56) References Cited

U.S. PATENT DOCUMENTS

| | | | | |
|---|---|---|---|---|
| 5,656,238 A | * | 8/1997 | Spencer ..................... | A61L 2/14 422/186.05 |
| 5,961,922 A | * | 10/1999 | Witte ......................... | A61L 2/24 422/292 |
| 9,508,531 B2 | * | 11/2016 | Kuribayashi ..... | H01J 37/32449 |

(Continued)

FOREIGN PATENT DOCUMENTS

| | | | |
|---|---|---|---|
| JP | 2002-249876 | 9/2002 | |
| JP | 2008-305953 | 12/2008 | |
| WO | WO 2014050744 A1 * | 4/2014 | ............. A23L 3/015 |

*Primary Examiner* — Atif Chaudry
(74) *Attorney, Agent, or Firm* — IPUSA, PLLC (57) ABSTRACT

An evacuation method used for a vacuum processing apparatus including a vacuum processing chamber is provided. The vacuum processing chamber is evacuated by an exhaust device for a first predetermined period of time by opening a valve connecting the exhaust device with the vacuum processing chamber. A pressure in the vacuum processing chamber is urged to increase by closing the valve and leaving the valve closed for a second predetermined period of time after evacuating the vacuum processing chamber. Evacuating the vacuum processing chamber and urging the pressure in the vacuum processing chamber to increase are performed so as to reduce the pressure in the vacuum processing chamber to a pressure between 6.7 Pa and $13.3 \times 10^2$ Pa (between 5 Torr and 10 Torr) without freezing moisture in the vacuum processing chamber.

7 Claims, 7 Drawing Sheets

(52) U.S. Cl.
CPC .............. *Y10T 137/86027* (2015.04); *Y10T 137/86083* (2015.04)

(56) References Cited

U.S. PATENT DOCUMENTS

| | | | |
|---|---|---|---|
| 2005/0058569 A1* | 3/2005 | Perlov | A01N 43/00 422/22 |
| 2008/0301972 A1* | 12/2008 | Yamawaku | H01J 37/3244 34/403 |
| 2014/0255251 A1* | 9/2014 | Kim | A61L 2/14 422/29 |
| 2015/0313250 A1* | 11/2015 | Itarashiki | A23L 3/015 426/231 |

* cited by examiner

EVACUATION METHOD AND VACUUM PROCESSING APPARATUS

CROSS-REFERENCE TO RELATED APPLICATIONS

This patent application is based upon and claims the benefit of priority of Japanese Patent Application No. 2014-263378, filed on Dec. 25, 2014, the entire contents of which are incorporated herein by reference.

BACKGROUND OF THE INVENTION

1. Field of the Invention

The present invention relates to an evacuation method and a vacuum processing apparatus.

2. Description of the Related Art

In vacuum processing apparatuses, a CD (Critical Dimension) control is performed to control a shift amount of a post-etching pattern dimension relative to a pre-etching mask dimension. However, in an etching process after maintenance for cleaning a vacuum chamber, a CD shift occurs in which a CD value deviates from a setting value. To solve this, it is proposed to perform the etching process after stabilizing an atmosphere in the vacuum chamber by seasoning the inside of the vacuum chamber after the cleaning, thereby preventing the CD shift from being generated. However, when performing the seasoning, a start of the etching process after the maintenance is delayed. Therefore, stable operation inside the vacuum chamber after the maintenance and reduction of a period of time until starting the etching process after the maintenance are desired.

In response to this, to reduce a period of time required to evacuate the vacuum chamber, a variety of evacuation methods are proposed. For example, Japanese Laid-Open Patent Application Publication No. 2002-249876 proposes a method of setting the inside of a chamber at a positive pressure state that is equal to or higher than the atmospheric pressure once by introducing an inactive gas into the chamber after starting an evacuation, and then further continuing the evacuation.

However, in the evacuation method of Japanese Laid-Open Patent Application Publication No. 2002-249876, when the pressure inside the vacuum chamber is reduced, moisture having attached to wall surfaces and surfaces of component parts that are exposed to the atmosphere during the maintenance, starts evaporating. After that, when the pressure inside the vacuum chamber continues to be reduced, the temperature of moisture decreases by adiabatic expansion eventually to a temperature lower than zero degrees C., and sometimes to a temperature between about −15 degrees C. to about −30 degrees C. At this time, moisture inside the vacuum chamber not having evaporated may freeze.

Frozen moisture continues to evaporate for a long time and traps moisture not yet frozen in small recesses in the wall surfaces and the like, thereby making it difficult to reduce a period of time of the evacuation. Moreover, the frozen moisture may cause a failure such as generation of particles, abnormal discharge, and corrosion of component parts.

SUMMARY OF THE INVENTION

Accordingly, to solve the above discussed problems, embodiments of the present invention aim to provide an evacuation method and a vacuum processing apparatus that reduce a pressure in a vacuum processing chamber to a predetermined pressure while preventing moisture inside the vacuum chamber from freezing.

According to one embodiment of the present invention, there is provided an evacuation method used for a vacuum processing apparatus including a vacuum processing chamber is provided. The vacuum processing chamber is evacuated by an exhaust device for a first predetermined period of time by opening a valve connecting the exhaust device with the vacuum processing chamber. A pressure in the vacuum processing chamber is urged to increase by closing the valve and leaving the valve closed for a second predetermined period of time after evacuating the vacuum processing chamber. Evacuating the vacuum processing chamber and urging the pressure in the vacuum processing chamber to increase are performed so as to reduce the pressure in the vacuum processing chamber to a pressure between 6.7 Pa and $13.3 \times 10^2$ Pa (between 5 Torr and 10 Torr) without freezing moisture in the vacuum processing chamber.

According to another embodiment of the present invention, there is provided a vacuum processing apparatus including a vacuum processing chamber. An exhaust device is connected to the vacuum processing chamber through a flow passage. A valve is provided in the flow passage and configured to open and close the flow passage. A control unit is configured to cause the valve to open and to cause the exhaust device to evacuate the vacuum processing chamber for a first predetermined period of time, and to cause the valve to close and be left closed for a second predetermined period of time after evacuating the vacuum processing chamber so as to urge a pressure in the vacuum processing chamber to increase. The control unit is configured to control the valve and the exhaust device so as to reduce the pressure in the vacuum processing chamber to a pressure between 6.7 Pa and $13.3 \times 10^2$ Pa (5 Torr and 10 Torr) without freezing moisture in the vacuum processing chamber.

Additional objects and advantages of the embodiments are set forth in part in the description which follows, and in part will become obvious from the description, or may be learned by practice of the invention. The objects and advantages of the invention will be realized and attained by means of the elements and combinations particularly pointed out in the appended claims. It is to be understood that both the foregoing general description and the following detailed description are exemplary and explanatory and are not restrictive of the invention as claimed.

DETAILED DESCRIPTION OF THE PREFERRED EMBODIMENTS

A description is given below of embodiments of the present invention, with reference to accompanying drawings. Note that elements having substantially the same functions or features may be given the same reference numerals and overlapping descriptions thereof may be omitted.

[Overall Configuration of Vacuum Processing Apparatus]

Figure 1:
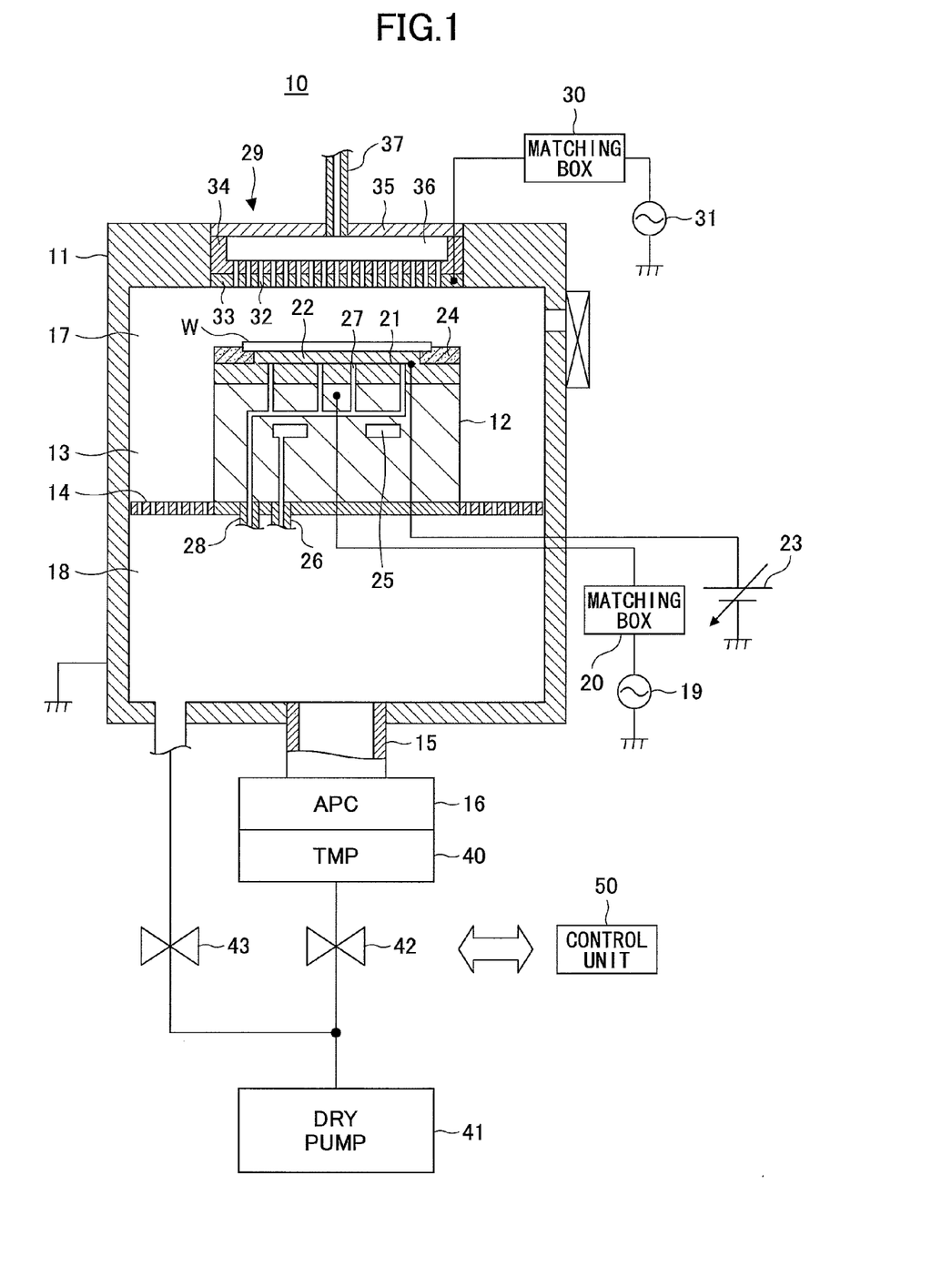
FIG. 1 is a vertical cross-sectional view of a vacuum processing apparatus according to an embodiment of the present invention.

To begin with, a description is given below of an example of an overall configuration of a vacuum processing apparatus 10 according to an embodiment of the present invention with reference to FIG. 1. In the embodiment, the vacuum processing apparatus 10 is an apparatus to generate plasma in a vacuum processing chamber 11 and perform a plasma process such as an etching process on a semiconductor wafer (which is hereinafter also referred to as a "wafer W") by an action of plasma.

The vacuum processing apparatus 10 is made of aluminum and the like, and includes a cylindrical vacuum processing chamber 11 that can seal the inside thereof. The vacuum processing chamber 11 is connected to a ground potential. The vacuum processing chamber 11 includes a pedestal 12 made of a conductive material, for example, aluminum and the like, thereinside. The pedestal 12 is a columnar support and also functions as a lower electrode.

An exhaust passage 13 that is a passage to evacuate a gas above the pedestal 12 out of the vacuum processing chamber 11 is formed between a side wall of the vacuum processing chamber 11 and a side surface of the pedestal 12. An evacuation plate 14 is provided in the middle of the exhaust passage 13. The evacuation plate 14 is a plate member having many holes, and functions as a partition plate that partitions the vacuum processing chamber 11 into an upper part and a lower part. The upper part of the vacuum processing chamber 11 divided by the evacuation plate 14 is a reaction chamber 17 in which a plasma process is performed. An exhaust pipe 15 for evacuating the gas inside the vacuum processing chamber 11 is connected to an evacuation chamber (manifold) 18 located at the lower part of the vacuum processing chamber 11. An APC (Adaptive Pressure Control: automatic pressure control) valve 16 is connected to the exhaust pipe 15. The evacuation plate 14 prevents the plasma generated in the reaction chamber 17 from leaking into the evacuation chamber 18 by trapping or reflecting the plasma. The exhaust pipe 15 is connected to a TEM (Turbo Molecular Pump) 40 and a dry pump (Dry Pump) 41 through the APC valve 16, and these exhaust devices evacuate the vacuum processing chamber 11 to reduce the pressure therein. More specifically, the dry pump 41 reduces the pressure inside the vacuum processing chamber 11 from the atmospheric pressure to a pressure in a degree of medium vacuum (e.g., equal to or lower than $1.3 \times 10$ Pa (0.1 Torr)). On this occasion, a valve 43 provided in a pipe (bypass route) connecting the dry pump 41 with the vacuum processing chamber 11 is opened, and a valve 42 provided in a pipe connecting the TMP 40 with the dry pump 41 is closed.

The TMP 40 reduces the pressure inside the vacuum processing chamber 11 to a high degree of vacuum (e.g., $1.3 \times 10^{-3}$ Pa ($1.0 \times 10^{-5}$ Torr)) that is lower than the medium degree of vacuum. On this occasion, the valve 43 is closed, and the valve 42 is opened.

A first high frequency power source 19 is connected to the pedestal 12 through a matching box 20, and for example, high frequency power for bias of, for example, 400 kHz to 13.56 MHz (which is also hereinafter referred to as "LF" (Low Frequency)) is supplied to the pedestal 12. The matching box 20 prevents the high frequency power from reflecting from the pedestal 12, and maximizes the supply efficiency of the high frequency power LF for bias to the pedestal 12.

An electrostatic chuck 22 containing an electrostatic electrode plate 21 therein is disposed on an upper surface of the pedestal 12. The electrostatic chuck 21 has a shape formed by stacking an upper disk-shaped member on a lower disk-shaped member. The upper disk-shaped member has a diameter smaller than a diameter of the lower disk-shaped member. The electrostatic chuck 22 is made of aluminum, and its upper surface is sprayed with ceramics and the like. When a wafer W is placed on the pedestal 12, the wafer W is placed on the upper disk-shaped member of the electrostatic chuck 22.

A direct current voltage source 23 is connected to the electrostatic electrode plate 21. When a positive DC voltage (which is also hereinafter referred to as a "HV" (High Voltage)) is applied to the electrostatic electrode plate 21, a negative potential is generated at a back surface of the wafer W (a surface on the side of the electrostatic chuck 22), and a voltage difference is generated between the electrostatic electrode plate 21 and the back surface of the wafer W. The wafer W is electrostatically attracted to and held on the upper disk-shaped member in the electrostatic chuck 22 by Coulomb's force or Johnson-Rahbeck force caused by the voltage difference.

Moreover, an annular focus ring 24 is placed on the electrostatic chuck 22 so as to surround a peripheral part of the wafer W. The focus ring 24 is made of conductive material, for example, silicon, and focuses plasma toward the surface of the wafer W in the reaction chamber 17, thereby improving the efficiency of the etching process.

Furthermore, an annular coolant chamber 25, for example, extending in a circumferential direction, is provided inside the pedestal 12. In the coolant chamber 25, a coolant having a low temperature, for example, cool water or Galden (Trademark) is supplied and circulated from a chiller unit through a coolant pipe 26. The pedestal 12 cooled by the coolant having the low temperature cools the wafer W and the focus ring 24 through the electrostatic chuck 22.

A plurality of heat transfer gas supply holes 27 are opened in a surface that attracts the wafer W thereon (attracting surface) of the upper disk-shaped member of the electrostatic chuck 22. A heat transfer gas such as helium (He) is supplied to the plurality of heat transfer gas supply holes 27 through a heat transfer gas supply line 28. The heat transfer gas is supplied to a gap between the attracting surface of the electrostatic chuck 22 and the back surface of the wafer W through the heat transfer gas supply holes 27. The heat transfer gas supplied to the gap transfers the heat of the wafer W to the electrostatic chuck 22.

A shower head 29 is disposed in a ceiling part of the vacuum processing chamber 11 so as to face the pedestal 12. A second high frequency power source 31 is connected to the shower head 29 through a matching box 30, and supplies high frequency power for plasma excitation of, for example, about 40 MHz (which is also hereinafter "HF" (High Frequency)). Thus, the shower head 29 also functions as an upper electrode. Here, the matching box 30 suppresses the high frequency power from reflecting from the shower head 29, and maximizes supply efficiency of the high frequency power HF for plasma excitation to the pedestal 12. Here, the second high frequency power source 31 and the matching box 30 may not be provided.

The shower head 29 includes a ceiling electrode plate 33 having many gas holes 32, a cooling plate 34 supporting the ceiling electrode plate 33 so as to cause the ceiling electrode plate 33 to hang from the cooling plate 34 detachably, and a lid body 35 to cover the cooling plate 34. A buffer chamber 36 is provided inside the cooling plate 34, and a gas introduction pipe 37 is connected to the buffer chamber 36. The shower head 29 supplies the gas supplied to the buffer chamber 36 from the gas introduction pipe 37 into the reaction chamber 17 through many of the gas holes 32.

The shower head 29 is detachable from and attachable to the vacuum processing chamber 11, and also functions as a lid of the vacuum processing chamber 11. By removing the shower head 29 from the vacuum processing chamber 11, a worker can directly touch the wall surfaces and component parts of the vacuum processing chamber 11. This makes it possible for the worker to clean the wall surfaces and the surfaces of the component parts of the vacuum processing chamber 11 and to remove extraneous matters attached to the wall surfaces and the like.

In the vacuum processing apparatus 10, the high frequency power LF for bias is supplied to the pedestal 12. The high frequency power HF for plasma excitation may be supplied or may not be supplied. By supplying at least the high frequency power HF for bias into the reaction chamber 17, plasma is generated from a gas supplied from the shower head 29, and a plasma process such as etching is performed on a wafer W by the plasma.

An operation of each component part of the vacuum processing apparatus 10 is controlled by a control unit 50 configured to control the entirety of the vacuum processing apparatus 10. The control unit 50 includes a CPU (Central Processing Unit), a ROM (Read Only Memory), a RAM (Random Access Memory) and the like, and controls the plasma process such as the etching process in accordance with a recipe setting a procedure of the plasma process and stored in the RAM and the like.

[Vapor Pressure Curve of Water]

Figure 2:
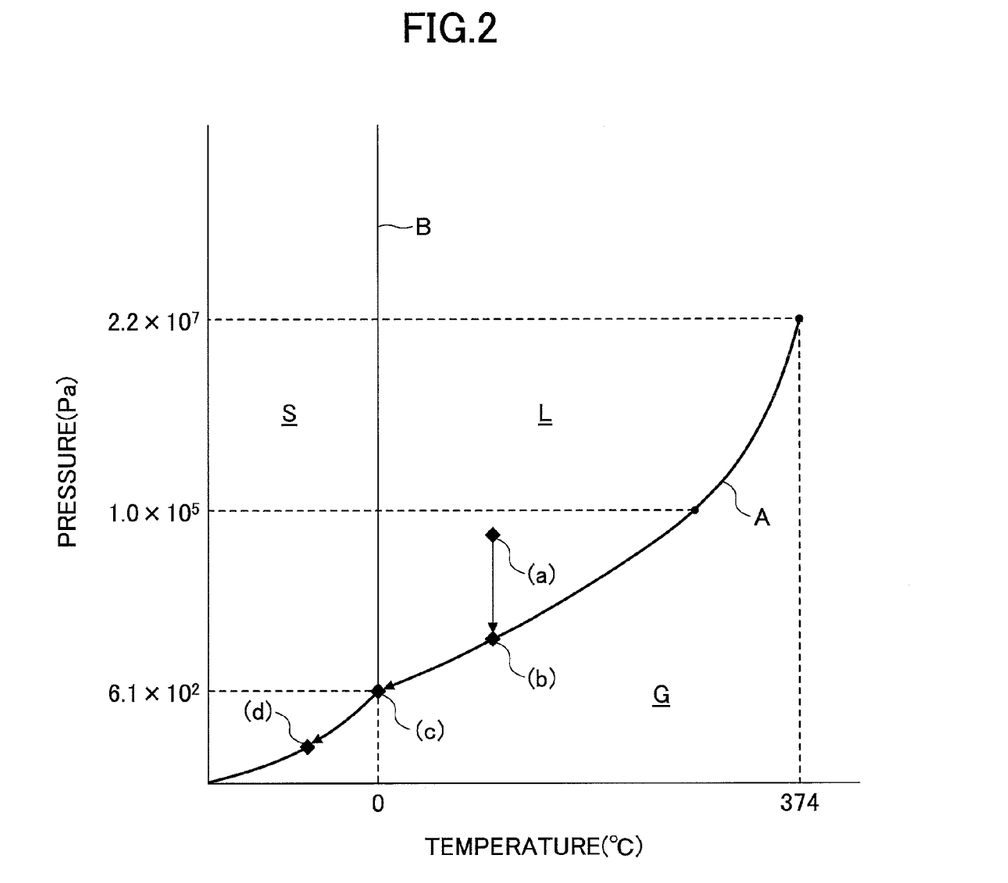
FIG. 2 is a graph showing a vapor pressure curve of water.

Next, a description is given below of solidification of water with reference to FIG. 2. FIG. 2 shows a vapor pressure curve of water. In FIG. 2, the horizontal axis shows a temperature, and the vertical axis shows a pressure. Moisture evaporates in an area G surrounded by a curve A and the horizontal axis. Water liquefies in an area L surrounded by the curve A and a straight line B. Water freezes in an area S surrounded by the curve A, a curve B and the vertical axis.

When an evacuation by the TMP 40 and the dry pump 41 starts from a state of gas remaining in the vacuum processing chamber 11 (point (a) in the area L) and the gas in the vacuum processing chamber 11 is evacuated, moisture attached to the wall surfaces and the like of the vacuum processing chamber 11 boils and evaporates (point (b) on the curve A). In particular, when the pressure in the vacuum processing chamber 11 rapidly decreases, moisture unexpectedly boils.

When the evacuation by the TMP 40 and the dry pump 41 continues, the pressure inside the vacuum processing chamber 11 further reduces. Because of this, the temperature decreases while moisture boils (from point (b) to point (c) on the curve A). Then, when the temperature becomes approximately zero degrees C. (point (c) on the curve A: triple point of water), moisture not having boiled yet freezes. When moisture freezes, bonds between water molecules become strong, and the evaporation of moisture becomes difficult even if the pressure is decreased. In other words, frozen moisture does not easily evaporate. When the pressure further reduces, the temperature decreases to a range from about −15 degrees C. to about −30 degrees C. (point (d) on the curve A). At this time, moisture not having evaporated yet may freeze.

Frozen moisture continues to boil for a long time, and traps unsolidified moisture in small recesses of wall surfaces and the like of the vacuum processing chamber 11. Due to this, frozen moisture makes it difficult to shorten a period of time required for the evacuation. Moreover, frozen moisture may cause generation of particles, abnormal discharge, corrosion of component parts and the like.

Therefore, as described below, the pressure in the vacuum processing chamber 11 is controlled so that a temperature becomes higher than zero degrees C. when the dry pump 41 evacuates the vacuum processing chamber 11 in the evacuation method according to an embodiment of the present invention. This causes the pressure in the vacuum processing chamber 11 to decrease to a reduced pressure state of $6.7–13.3\times10^2$ Pa (5-10 Torr) from the atmospheric pressure immediately after the maintenance while preventing moisture attached to the wall surfaces and the like of the vacuum processing chamber 11 from freezing.

[Evacuation Method]

Figure 3:
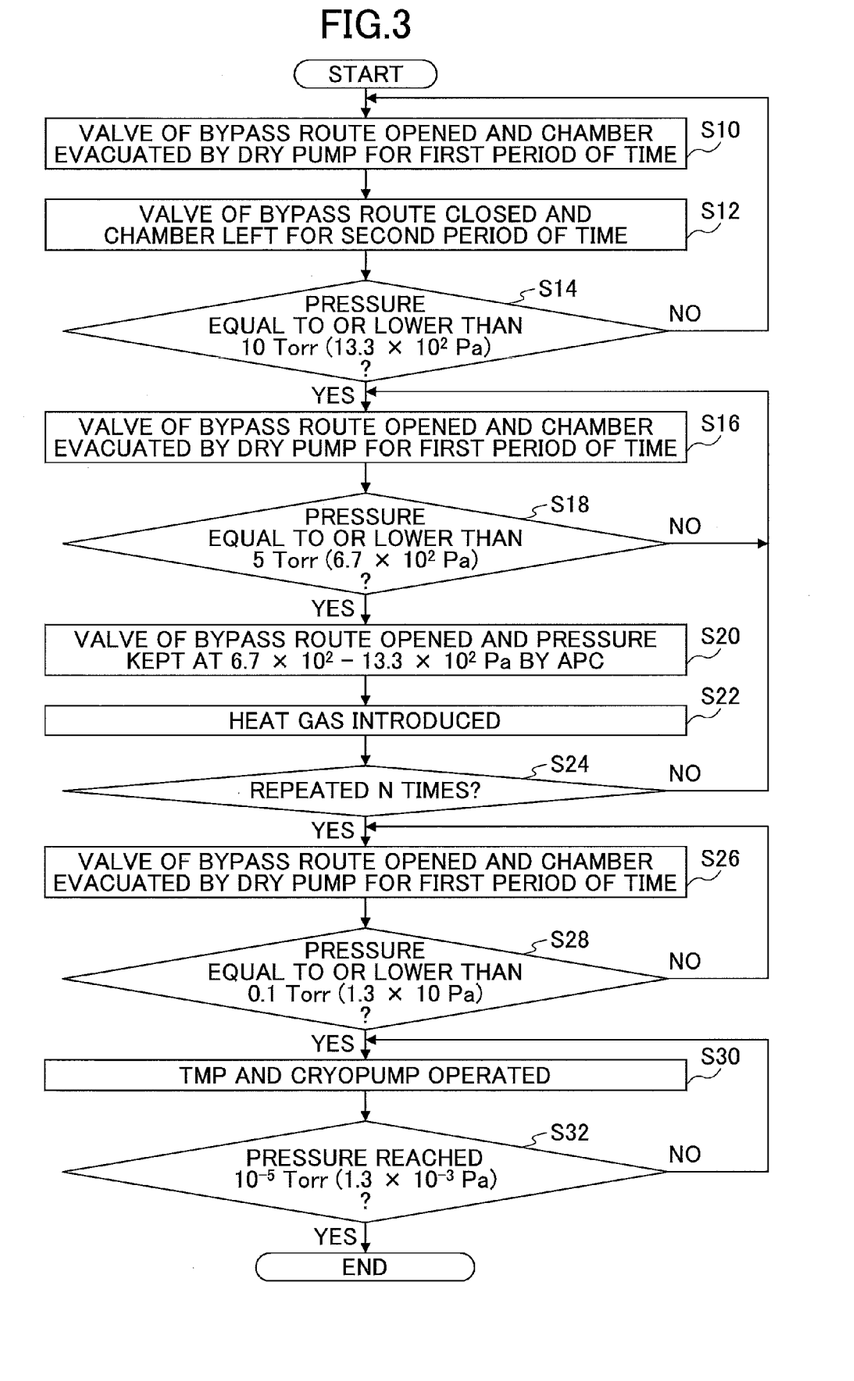
FIG. 3 is a flowchart illustrating an example of an evacuation process according to embodiments of the present invention.
Figure 4:
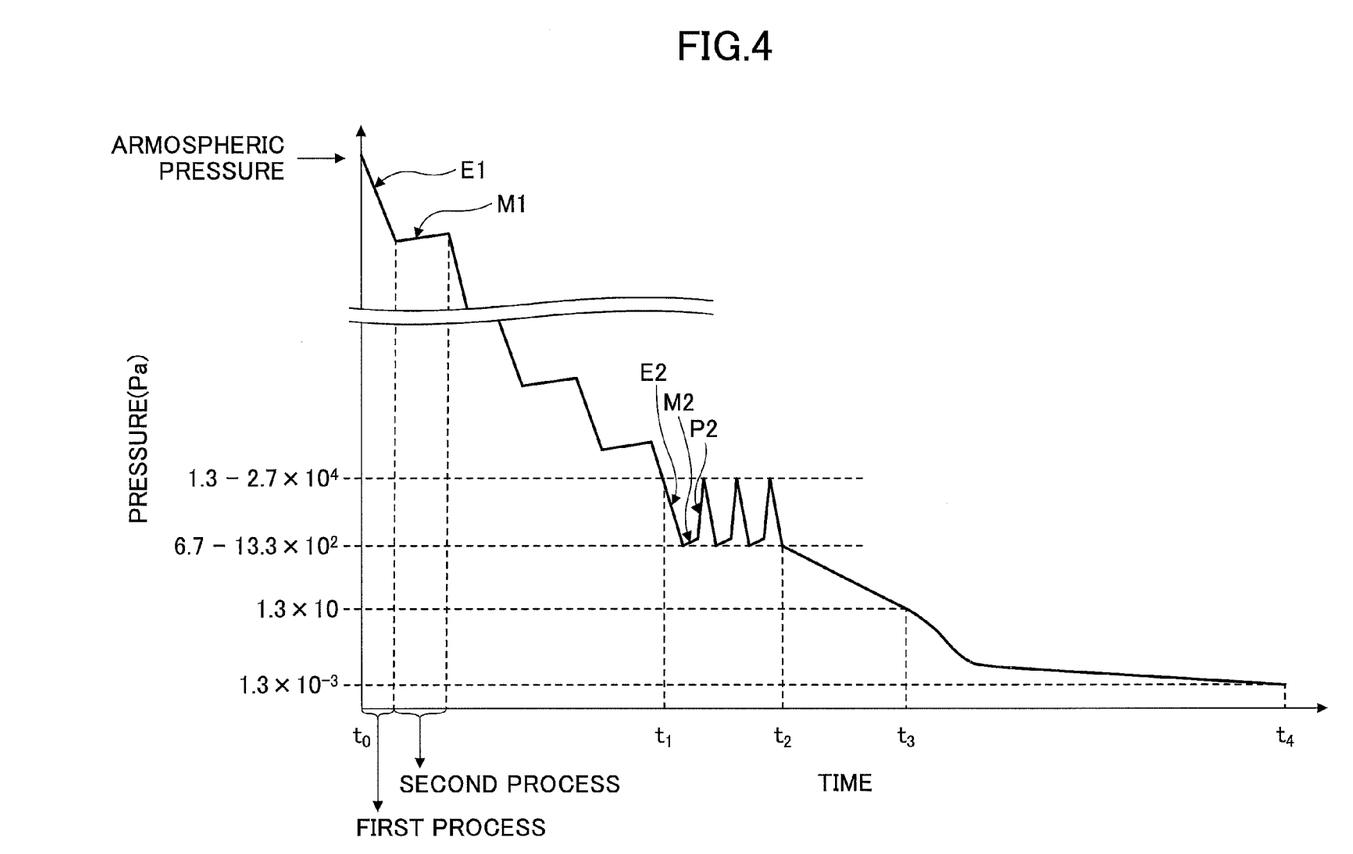
FIG. 4 is a graph illustrating an example of a pressure transition inside a vacuum chamber according to an embodiment of the present invention.

Next, a description is given below of the evacuation method according to an embodiment of the present invention with reference to FIGS. 3 and 4. FIG. 3 is a flowchart illustrating an example of the evacuation process according to the embodiment. FIG. 4 illustrates an example of a pressure transition in the vacuum processing chamber 11 of the evacuation according to the embodiment. In FIG. 4, the horizontal axis indicates time after starting the evacuation (time $T_0$), and the vertical axis indicates a pressure in the vacuum processing chamber 11. The evacuation method according to the embodiment is performed after cleaning the wall surfaces and the like of the vacuum processing chamber 11 in order to remove a reaction product attached thereto when an etching process is performed in the vacuum processing chamber 11. Here, when starting the evacuation process of the embodiment, the valve 42 provided between the TMP 40 and the dry pump 41 is closed.

In the evacuation method according to the embodiment, to begin with, the control unit 50 controls the valve 43 of the bypass route so as to open. This causes the dry pump 41 to be in communication with the vacuum processing chamber 11. The dry pump 41 evacuates the vacuum processing chamber 11 for a first predetermined period of time (step S10: first process). As illustrated in FIG. 4, this causes the pressure in the vacuum processing chamber 11 to be reduced by a predetermined amount in the first process shown by E1 from the atmospheric pressure at time $T_0$ when the evacuation is started. The first predetermined period of time may be, for example, from tens of seconds to a few or several minutes.

Here, when the pressure is rapidly reduced by continuing the evacuation as it is, the temperature decreases while moisture is boiling, and moisture not having evaporated freezes when the temperature becomes approximately zero degrees C. Therefore, in the evacuation method in FIG. 3, the control unit 50 controls the valve 43 so as to close once after the elapse of the first predetermined period of time (after the first process), and urges the pressure in the vacuum processing chamber 11 to naturally increase by leaving the valve 43 for a second predetermined period of time (step S12: second process). This causes the valve 43 to naturally leak a gas in the second process shown by M1 in FIG. 4, thereby increasing the pressure in the vacuum processing chamber 11. The second predetermined period of time may be, for example, a few or several minutes to about ten minutes.

Subsequently, the control unit 50 determines whether the pressure in the vacuum processing chamber 11 is equal to or lower than 10 Torr ($13.3 \times 10^2$ Pa) (step S14). When the pressure in the vacuum processing chamber 11 is higher than 10 Torr, the first process (step S10) and the second process (step S12) are performed again, and steps S10 through S14 are repeated until the pressure in the vacuum processing chamber 11 is equal to or lower than 10 Torr at step S14.

Next, when determining that the pressure in the vacuum processing chamber 11 is equal to or lower than 10 Torr, the control unit 50 controls the valve 43 of the bypass route to open. This causes the dry pump 41 to be in communication with the vacuum processing chamber 11. The dry pump 41 evacuates the vacuum processing chamber 11 (step S16). Next, the control unit 50 determines whether the pressure in the vacuum processing chamber 11 is equal to or lower than 5 Torr (6.7 Pa) (step S18). When determining that the pressure in the vacuum processing chamber 11 is higher than 5 Torr, by returning to step S16, the control unit 50 causes the dry pump 41 to maintain the evacuation. This causes the pressure in the vacuum processing chamber 11 to be reduced (E2 in FIG. 4).

On the other hand, determining that the pressure in the vacuum processing chamber 11 is equal to or lower than 5 Torr, the control unit 50 causes the valve 43 of the bypass route to close, and also causes the valve 42 to open. This causes the pressure in the vacuum processing chamber 11 to be maintained at 5-10 Torr ($6.7$–$13.3 \times 10^2$ Pa) by adjusting a degree of openness of the APC valve 16 in the evacuation by the dry pump 41 (step S20: M2 in FIG. 4). This causes the pressure in the vacuum processing chamber 11 to be maintained at 5-10 Torr.

Next, the control unit 50 introduces a heating gas into the vacuum processing chamber 11 (step S22). An inactive gas such as He gas and Ar gas is cited as an example of the heating gas. This causes the pressure in the vacuum processing chamber 11 to be rapidly increased (P2 in FIG. 4).

Subsequently, when the pressure in the vacuum processing chamber 11 is rapidly increased to a range from 100 Torr to 200 Torr ($1.3 \times 10^4$ Pa to $2.7 \times 10^4$ Pa), the temperature of the atmosphere in the vacuum processing chamber 11 is increased by adiabatic expansion. This causes moisture attached to the wall surfaces and the like of the vacuum processing chamber 11 to be heated, thereby increasing the temperature of moisture. Hence, for example, even if the temperature of moisture decreases to the neighborhood of the triple point temperature of water due to the adiabatic expansion while the pressure in the vacuum processing chamber 11 is maintained at 5-10 Torr, the temperature of moisture can be prevented from being lower than the triple point temperature.

Subsequently, in step S24 of FIG. 3, the control unit 50 determines whether steps S16 through S22 are repeated N times. A repeat count N is preliminarily determined. In FIG. 4, the repeat count N is three.

A description is given with reference to FIG. 3 again. After steps S16 through S22 are repeated N times, the process advances to step S22, and the control unit 50 opens the valve 43 of the bypass route so as to cause the dry pump 41 to continue to evacuate the vacuum processing chamber 11 (time $t_2$ to $t_3$ in FIG. 3).

Next, the control unit 50 determines whether the pressure in the vacuum processing chamber 11 is equal to or lower than 0.1 Torr ($1.3 \times 10$ Pa) (step S28). When determining that the pressure in the vacuum processing chamber 11 is equal to or lower than 0.1 Torr, the control unit 50 causes the TMP 40 to operate, and after that (at and after time $t_3$), causes a cryopump to operate while the dry pump 41 and the TMP 40 continues to evacuate the vacuum processing chamber 11 (step S30). The cryopump reduces a partial pressure of moisture in the vacuum processing chamber 11. Subsequently, the control unit 50 determines whether the pressure in the vacuum processing chamber 11 has reached a target pressure of $1 \times 10^{-5}$ Torr ($1.3 \times 10^{-3}$ Pa) (step S32). When the control unit 50 determines that the pressure in the vacuum processing chamber 11 has reached the target pressure of $1 \times 10^{-5}$ Torr ($1.3 \times 10^{-3}$ Pa), the process ends (time $t_4$ in FIG. 4).

The pressure of the triple point on the vapor pressure curve (point (c) on the curve A in FIG. 2), which is a critical point at which the temperature of moisture decreases due to the adiabatic expansion while boiling and the moisture freezes, is 4.6 Torr ($6 \times 10^2$ Pa). Accordingly, as long as the pressure in the vacuum processing chamber 11 is controlled so as to become 5 Torr or higher, moisture in the vacuum processing chamber 11 does not freeze.

In the evacuation method of the present embodiment, the first process and the second process are provided. In the first process, the vacuum processing chamber 11 is evacuated by opening the valve 43 of the bypass route. On this occasion, the temperature in the vacuum processing chamber 11 decreases along with the decrease of the pressure in the vacuum processing chamber 11. When the temperature in the vacuum processing chamber 11 becomes lower than zero degrees C., moisture in the vacuum processing chamber 11 freezes. Therefore, the second process is performed before the pressure in the vacuum processing chamber 11 becomes 5 Torr that is higher than the pressure of the triple point on the vapor pressure curve of water. In the second process, the valve 43 is closed and left. On this occasion, even when the valve 43 is closed, the vacuum processing chamber 11 does not completely get blocked due to machining accuracy of the valve 43 and its surroundings. Thus, the pressure on the vacuum processing chamber 11 gradually increases, and the temperature in the vacuum processing chamber 11 gradually increases along therewith.

In this manner, in the evacuation method of the embodiment, the first process and the second process are provided, thereby gently evacuating the vacuum processing chamber 11. This enables the pressure in the vacuum processing chamber 11 to slowly decrease in stages as illustrated in FIG. 4. For example, a manner of decreasing the pressure from time $t_0$ to $t_1$ of FIG. 4 is a proposed portion of the evacuation method of the embodiment, which shows a manner of slowly evacuating the vacuum processing chamber 11 so that the pressure in the vacuum processing chamber 11 does not become lower than the triple point pressure as a result of repetition of the first process and the second process. Thus, according to the evacuation method of the embodiment, the pressure in the vacuum processing chamber 11 can be reduced to the pressure of 5-10 Torr from the atmospheric pressure by gradually reducing the pressure in the vacuum processing chamber 11. On this occasion, the evacuation is slowly performed so that the temperature in the vacuum processing chamber 11 does not become lower than zero degrees C. Because of this, moisture attached to the wall surfaces and the like of the vacuum processing chamber 11 and not having evaporated yet does not freeze. Accordingly, the evaporation of moisture attached to the wall surfaces and the like of the vacuum processing chamber 11 can be continued, thereby accelerating the discharge from the vacuum processing chamber 11.

Here, as illustrated in FIG. 4, a purge process that introduces a heating gas shown by P2 and is performed for a period from time $t_1$ to time $t_2$ is not performed for a period from time $t_0$ to time $t_1$ when the first process and the second process are repeated. This is because the temperature rises too high due to the purge process. Here, the first process and the second process may be repeated, or may be performed once.

(Conditions of Moisture)

A description is given below of conditions of moisture in the vacuum processing chamber 11 while performing the evacuation method according to an embodiment of the present invention, with reference to FIG. 5. Each curve C and D of FIG. 5 indicates an amount of moisture (emission intensity of an OH group) in the vacuum processing chamber 11 of the evacuation method according to the embodiment. Each curve A and B of FIG. 5 indicates an amount of moisture (emission intensity of an OH group) in the vacuum processing chamber 11 of a comparative example of performing continuous evacuation.

The curve A indicates the amount of moisture in the vacuum processing chamber 11 by using the emission intensity of the OH group when the pressure in the vacuum processing chamber 11 is reduced to any pressure between 5 Torr and 10 Torr from the atmospheric pressure for a shorter time (e.g., 30 seconds) than the evacuation of the embodiment.

Figure 6A:
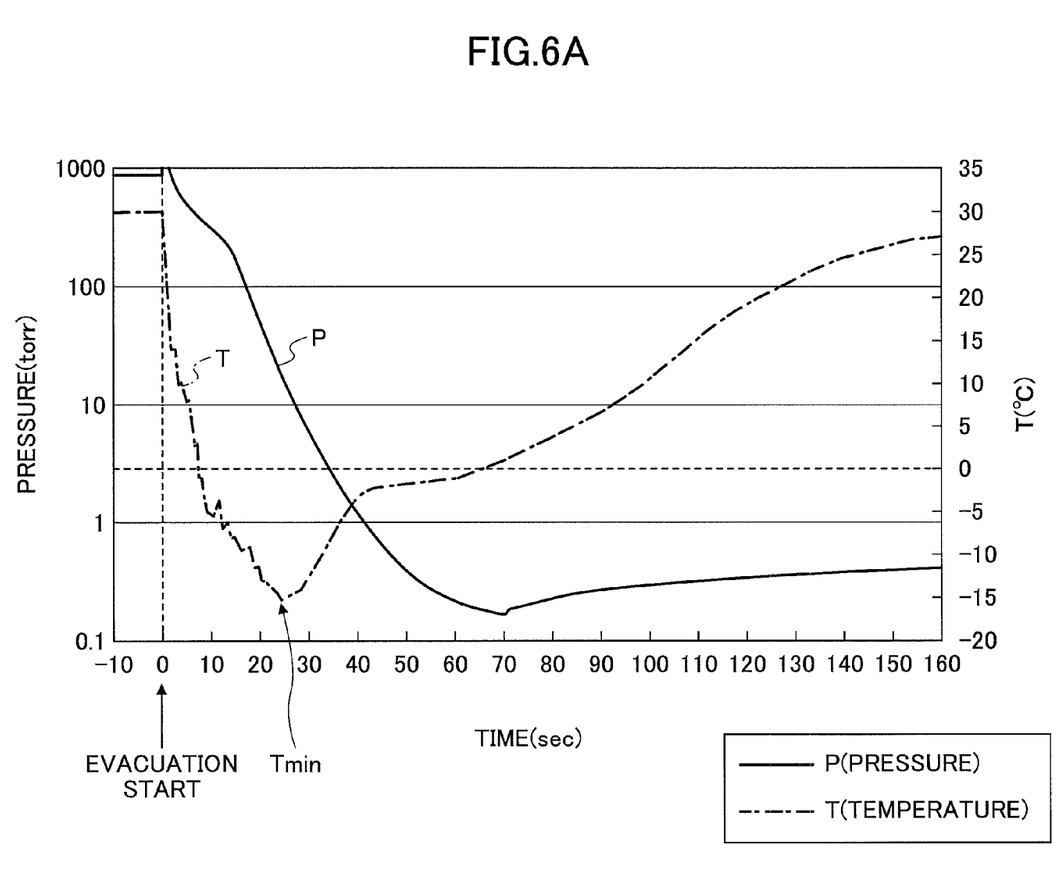
FIGS. 6A and 6B are transition diagrams of pressures and temperatures of evacuations according to an embodiment of the present invention and a comparative example.

For example, a description is given below of conditions of the pressure and the temperature in the vacuum processing chamber 11 when performing the evacuation method of the embodiment with reference to FIGS. 6A and 6B.

In the comparative examples, the dry pump 41 continuously evacuates the vacuum processing chamber 11, and the pressure in the vacuum professing chamber 11 is rapidly reduced. This causes the temperature in the vacuum processing chamber 11 to rapidly decrease. As a result, because a minimum temperature Tmin in the vacuum processing chamber 11 decreases to about −15 degrees C. during the evacuation, moisture in the vacuum processing chamber 11 freezes.

The curve B is the emission intensity of the OH group when the pressure in the vacuum processing chamber 11 is reduced to 5-10 Torr for a shorter time of 75 seconds than the evacuation of the embodiment. The curves A and B are the emission intensities when continuously evacuating the vacuum processing chamber 11 (i.e., when the second process of the embodiment is not present).

The curve C indicates the pressure in the vacuum processing chamber 11 by using the emission intensity of the OH group when the pressure in the vacuum processing chamber 11 is reduced to 5-10 Torr in 30 minutes according to the evacuation method of the embodiment. The curve D indicates the pressure in the vacuum processing chamber 11 by using the emission intensity of the OH group when the pressure in the vacuum processing chamber 11 is reduced to 5-10 Torr in 60 minutes according to the evacuation method of the embodiment.

Figure 5:
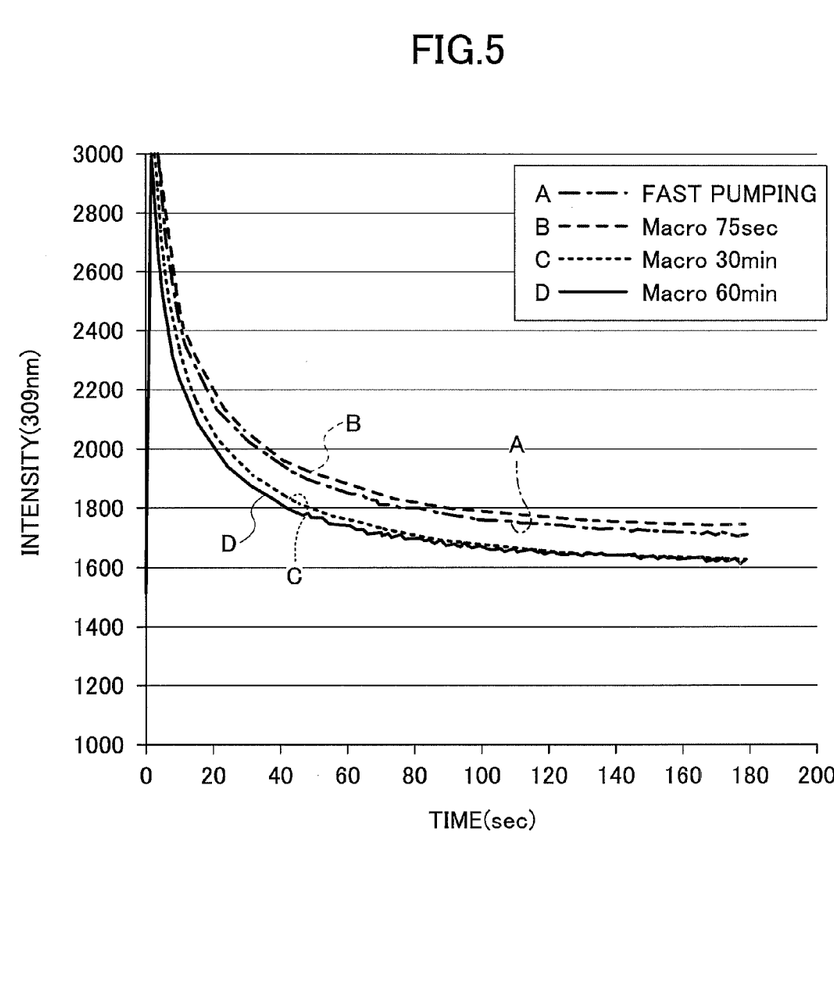
FIG. 5 is a graph showing amounts of moisture (emission intensities of an OH group) of evacuations according an embodiment of the present invention and a comparative example.
Figure 6B:
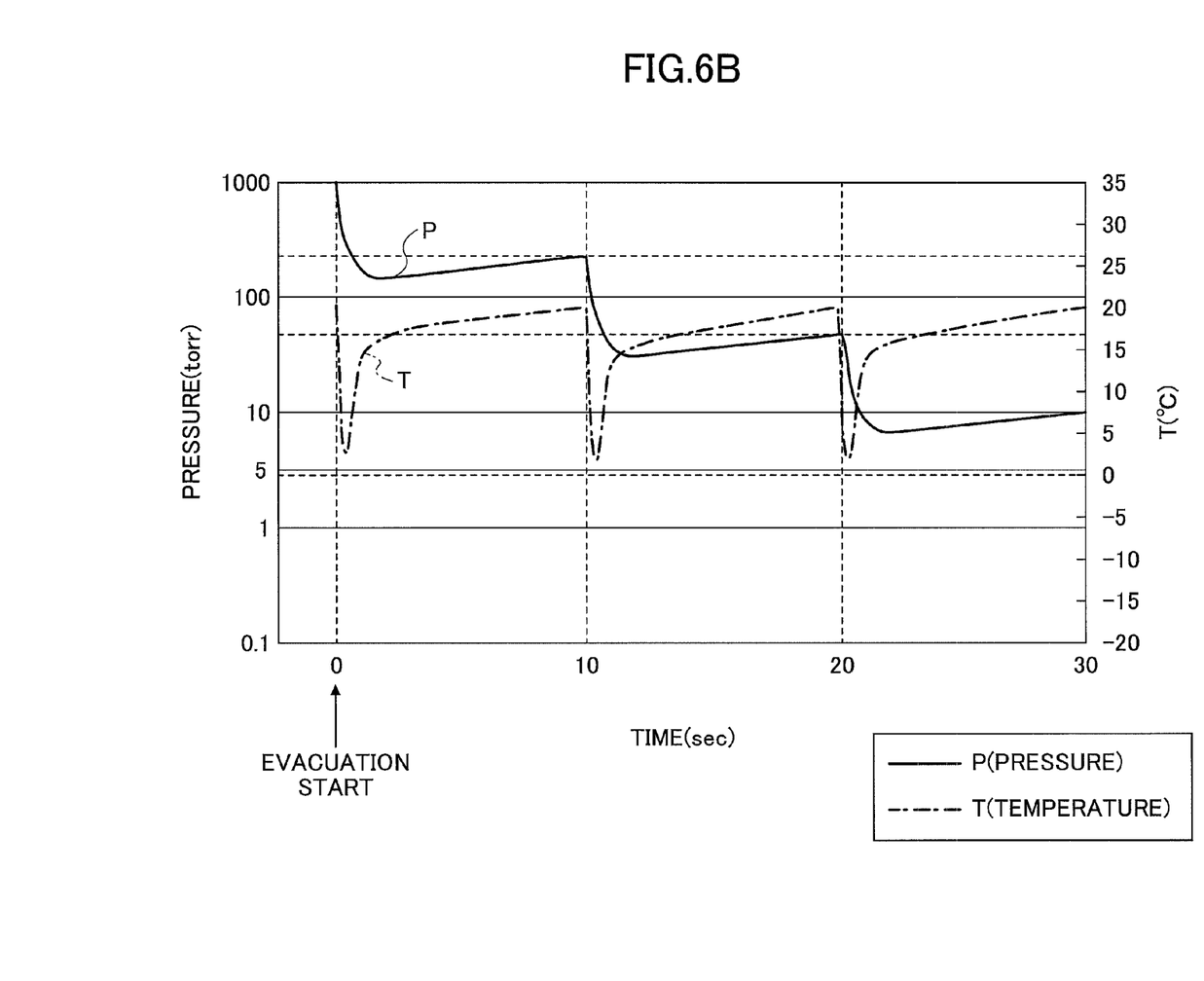

In FIG. 6B, the evacuation method of the embodiment is performed to obtain the curve C of FIG. 5. In FIG. 6B, the pressure in the vacuum processing chamber 11 can be reduced to 5-10 Torr by repeating the first process and the second process three times.

On this occasion, in the evacuation method of the embodiment, the pressure in the vacuum processing chamber 11 decreases at a rate of 3333 to 3350 Pa (25.0 to 25.2 Torr) per minute by performing the first process and the second process. This prevents the temperature in the vacuum processing chamber 11 from rapidly decreasing. As a result, the minimum temperature in the vacuum processing chamber 11 does not become lower than zero degrees C. during the evacuation, and the solidification of moisture in the vacuum processing chamber 11 can be prevented.

The emission intensities shown in FIG. 5 indicate that the number of the OH groups in the vacuum processing chamber 11 according to the evacuation method of the embodiments is fewer than the evacuation method of the comparative examples, and the amounts of moisture of the embodiments are also smaller than those of the comparative examples. In the curves C and D, most of the OH groups disappear by performing the evacuation for about 30 minutes, and moisture in the vacuum processing chamber 11 is unlikely to freeze.

As described above, according to the evacuation method of the embodiments, a pressure in a vacuum processing chamber can be reduced to a predetermined pressure so as not to freeze moisture in the vacuum processing chamber. This causes moisture attached to a wall surface and the like of the vacuum processing chamber 11 and not yet evaporated not to freeze during the evacuation. Hence, the evaporation of moisture attached to the wall surfaces and the like of the vacuum processing chamber 11 can be continued, thereby accelerating the discharge of moisture from the vacuum processing chamber 11 and shortening the evacuation time.

In this manner, according to the embodiments of the present invention, a pressure in a vacuum processing chamber can be reduced to a predetermined pressure without freezing moisture in the vacuum processing chamber.

Hereinabove, although the evacuation method and the vacuum processing apparatus have been described according to the embodiments, the evacuation method and the vacuum processing apparatus of the present invention is not limited to the embodiments and various modifications and improvements can be made without departing from the scope of the invention. Moreover, the embodiments and modifications can be combined as long as they are not contradictory to each other.

For example, the vacuum processing apparatus to implement the evacuation method according to the embodiments of the present invention may be applied to a capacitively coupled plasma (CCP: Capacitively Coupled Plasma) apparatus, an inductively coupled plasma (ICP: Inductively Coupled Plasma) apparatus, a CVD (Chemical Vapor Deposition) apparatus using a radial line slot antenna, a helicon wave excited plasma (HWP: Helicon Wave Plasma) apparatus, an electron cyclotron resonance plasma (ECR: Electron Cyclotron Resonance Plasma) apparatus and the like.

A substrate to be processed in the plasma processing apparatus of the present invention is not limited to the wafer, but for example, may be a large substrate for a flat panel display, a substrate for an EL (electroluminescence) device or a solar cell.

Here, the vacuum processing chamber of the vacuum processing apparatus according to the embodiments of the present invention is made of aluminum, and a surface of aluminum is alumited (anodized). Many hollows are present in an almited (anodized) film of the vacuum processing chamber, and moisture is accumulated in the hollows. Hence, when predetermined parts are provided adjacent to the inner wall of the vacuum processing chamber, moisture in the hollows is unlikely to discharge as a gas. In other words, the evacuation method according to the embodiments of the present invention is more effectively applied to a vacuum processing chamber having a complicated inner structure.

What is claimed is:

1. An evacuation method used for a vacuum processing apparatus including a vacuum processing chamber, the method comprising steps of:
    evacuating the vacuum processing chamber for a first predetermined period of time by an exhaust device by opening a valve connecting the exhaust device with the vacuum processing chamber; and
    urging a pressure in the vacuum processing chamber to increase by closing the valve and leaving the valve closed for a second predetermined period of time after the step of evacuating the vacuum processing chamber; and
    repeating a series of steps including the step of evacuating the vacuum processing chamber and the step of urging the pressure in the vacuum processing chamber to increase until the pressure in the vacuum processing chamber reaches a pressure between 6.7 and $13.3 \times 10^2$ Pa (between 5 Torr and 10 Torr) for the first time, wherein in each subsequent repetition of the series of steps, the minimum pressure reached is lower than the minimum pressure reached during the previous repetition of the series of steps.

2. The method as claimed in claim 1, wherein the pressure in the vacuum processing chamber decreases at a rate of 3333 to 3359 Pa (25.0 to 25.2 Torr) per minute by performing the steps of evacuating the vacuum processing chamber and urging the pressure in the vacuum processing chamber to increase.

3. The method as claimed in claim 1, wherein the pressure in the vacuum processing chamber is reduced from an atmospheric pressure to the pressure between 6.7 and $13.3 \times 10^2$ Pa (between 5 Torr and 10 Torr).

4. A vacuum processing apparatus, comprising:
    a vacuum processing chamber;
    an exhaust device connected to the vacuum processing chamber through a flow passage;
    a valve provided in the flow passage and configured to open and close the flow passage; and
    a control unit configured to perform a first operation of causing the valve to open and causing the exhaust device to evacuate the vacuum processing chamber for a first predetermined period of time, and a second operation of causing the valve to close and be left closed for a second predetermined period of time after evacuating the vacuum processing chamber so as to urge a pressure in the vacuum processing chamber to increase, the control unit being configured to repeat a series of operations including the first operation to evacuate the vacuum processing chamber and the second operation to urge the pressure in the vacuum processing chamber to increase until the pressure in the vacuum processing chamber reaches a pressure between 6.7 and $13.3 \times 10^2$ Pa (between 5 Torr and 10 Torr) for the first time, wherein in each subsequent repetition of the series of operations, the minimum pressure reached is lower than the minimum pressure reached during the previous repetition of the series of operations.

5. The vacuum processing apparatus as claimed in claim 4, wherein the control unit alternately repeats the first operation and the second operation.

6. The vacuum processing apparatus as claimed in claim 4, wherein the pressure in the vacuum processing chamber decreases at a rate of 3333 to 3359 Pa (25.0 to 25.2 Torr) per minute by performing the first operation and the second operation.

7. The vacuum processing apparatus as claimed in claim 4, wherein the pressure in the vacuum processing chamber is reduced from an atmospheric pressure to the pressure between 6.7 and $13.3 \times 10^2$ Pa (between 5 Torr and 10 Torr).

* * * * *